(12) United States Patent
Dam-Huisman

(10) Patent No.: US 12,343,286 B2
(45) Date of Patent: Jul. 1, 2025

(54) VITRECTOME ACTUATOR

(71) Applicant: Crea IP B.V., Vierpolders (NL)

(72) Inventor: Adriaantje Coliene Dam-Huisman, Delfgauw (NL)

(73) Assignee: Crea IP B.V., Vierpolders (NL)

( * ) Notice: Subject to any disclaimer, the term of this patent is extended or adjusted under 35 U.S.C. 154(b) by 950 days.

(21) Appl. No.: 17/285,517

(22) PCT Filed: Nov. 14, 2019

(86) PCT No.: PCT/NL2019/050741
§ 371 (c)(1),
(2) Date: Apr. 15, 2021

(87) PCT Pub. No.: WO2020/101489
PCT Pub. Date: May 22, 2020

(65) Prior Publication Data
US 2021/0386587 A1 Dec. 16, 2021

(30) Foreign Application Priority Data
Nov. 16, 2018 (NL) ........................................ 2022011

(51) Int. Cl.
*A61F 9/007* (2006.01)
(52) U.S. Cl.
CPC .................. *A61F 9/00763* (2013.01)
(58) Field of Classification Search
CPC ...... A61B 17/320016; A61B 17/32002; A61B 17/320024; A61B 17/320028;
(Continued)

(56) References Cited

U.S. PATENT DOCUMENTS 5,284,472 A * 2/1994 Sussman ............. A61F 9/00763
606/171
5,980,546 A * 11/1999 Hood ............. A61B 17/320016
606/171
(Continued)

FOREIGN PATENT DOCUMENTS

JP 2010057642 3/2010
WO WO-2007110259 A1 * 10/2007 ......... A61B 1/00158

*Primary Examiner* — Katherine H Schwiker
*Assistant Examiner* — Zehra Jaffri
(74) *Attorney, Agent, or Firm* — N.V. Nederlandsch Octrooibureau

(57) ABSTRACT

An actuation system for an ophthalmic cutting tool is disclosed. The system comprises a chamber (44) separated by a diaphragm (46) into a first compartment (48) a second compartment (50). A first port (49) is provided in fluid communication with the first compartment (48) and a first conduit (38) connected to the ophthalmic cutting tool and a second port (51) is provided in fluid communication with the second compartment (50) and a second conduit (40) connected to the ophthalmic cutting tool. The diaphragm (46) is movably mounted within the chamber (44) and is configured for alternate movement between a first position and a second position to alternately increase and decrease the volume of the first and second compartments. A drive system (54) is provided to drive oscillation of a diaphragm actuator (52) for moving the diaphragm between the first and second positions.

21 Claims, 7 Drawing Sheets

(58) Field of Classification Search
CPC .... A61B 17/32004; A61B 2017/00539; A61B 2017/00544; A61B 2017/00548; A61B 2017/00535; A61F 9/00763; A61F 9/00736

See application file for complete search history.

(56) References Cited

U.S. PATENT DOCUMENTS

| | | | |
|---|---|---|---|
| 10,893,978 B2 * | 1/2021 | Sawicz | A61F 9/00763 |
| 2007/0088376 A1 * | 4/2007 | Zacharias | A61B 17/32002 606/169 |
| 2007/0225781 A1 * | 9/2007 | Saadat | A61F 7/12 607/105 |
| 2009/0082715 A1 * | 3/2009 | Charles | A61F 9/00763 606/171 |
| 2009/0131832 A1 * | 5/2009 | Sacristan Rock | A61B 17/3401 600/587 |
| 2010/0145374 A1 | 6/2010 | Perkins et al. | |
| 2011/0144675 A1 * | 6/2011 | Gao | A61F 9/00736 606/167 |
| 2011/0295293 A1 * | 12/2011 | Agahi | A61F 9/00763 606/167 |
| 2012/0158030 A1 * | 6/2012 | Underwood | A61B 17/320783 606/171 |
| 2012/0165724 A1 * | 6/2012 | Auld | A61F 9/00763 604/22 |
| 2018/0243134 A1 | 8/2018 | Dean et al. | |

* cited by examiner

VITRECTOME ACTUATOR

FIELD OF THE INVENTION

The invention relates to an actuation system for an ophthalmic cutting tool, such as a vitrectomy tool.

BACKGROUND OF THE INVENTION

Ophthalmic surgical procedures for the removal of tissue from the eye require small, precise surgical cutting instruments. Vitrectomy is a surgical procedure in which vitreous humour is removed from within the eye ball. Such a procedure may be indicated or required in cases of retinal detachment, vitreous entanglement with an intraocular lens, clouded or bloodied humour, or other ocular complaints in which removal of some or all of the vitreous humour is indicated.

Known vitrectomy devices can comprise a hollow, reciprocating cutting blade and a sheath, one disposed within the other.

U.S. Pat. No. 5,106,364 describes a known ophthalmic surgical cutting instrument comprising an outer tubular member with a closed distal end, an aperture adjacent to the closed distal end and an inner tube slidably disposed within the outer tube. The inner tube reciprocates between first and second positions, and as tissue is drawn into the inner tube via suction, the reciprocation of the cutting member severs the tissue so that it can be aspirated through the inner tubular member.

United States Patent Application Publication No. US2012/310146 describes a system for conducting vitrectomy, which includes a gas source, a vitrector including a cutting mechanism that opens and closes according to a pressure at the vitrector and a pulse generating system receiving gas from the gas source and generating pulses at the vitrector. The pulses cause the pressure at the vitrector to vary according to a cycle, and the varying pressure at the vitrector causes the cutting mechanism of the vitrector to open and close.

Known vitrectomy tools and associated pneumatic control systems suffer from high gas consumption, high noise levels during operation, and sub-optimal response times for the cutting tool. The present invention seeks to provide an improved actuation system for an ophthalmic surgical cutting tool that overcomes problems associated with known systems and devices.

US patent publication US2018/243134 discloses a handheld reciprocating surgical tool, having a diaphragm assembly to drive a cutting tool, as well as an inertial damper. The diaphragm assembly 304 is pneumatically driven.

Japanese patent publication JP-2010-057642 discloses an apparatus for vitreous body surgery, which is pneumatically driven.

US patent publication US2010/145374 discloses a system for operating and controlling pneumatically driven vitrectomy probes. An enclosed pressure chamber is provided with a pressure transducer, allowing control of pressure level to the enclosed pressure chamber. The actuator of the cutting tool is provided with a biasing spring for backward motion.

SUMMARY OF THE INVENTION

In a first aspect of the present invention, there is provided an actuation system for an ophthalmic cutting tool comprising a chamber fluidically separated by a diaphragm into a first compartment defining a first internal volume and a second compartment defining a second internal volume. A first port is provided in fluid communication with the first compartment and is configured for connection to a first conduit connected to a handheld ophthalmic cutting tool. A second port is provided in fluid communication with the second compartment, and is configured for connection to a second conduit connected to the ophthalmic cutting tool.

The diaphragm is movably mounted within the chamber and is configured for alternate movement between a first position and a second position, such that movement from the first position to the second position decreases the first volume and increases the second volume. It will be understood that as the volume of the first compartment increases, the volume of the second chamber decreases and vice versa.

To move the diaphragm back and forth within the chamber to alternately vary the volume of the first and second compartments, a diaphragm actuator is coupled to the diaphragm and is configured to oscillate back and forth to move the diaphragm between the first position and the second position. A drive system is configured to drive the oscillation of the diaphragm actuator.

In a second aspect of the invention, first and second variable volume compartments can be fluidically separated from each other by two diaphragms. These aspects operate according to the same principle as the first aspect of the invention because the oscillation of the first and second diaphragms can be driven by a common drive system. In the second aspect of the invention, there is provided an actuation system for an ophthalmic cutting tool comprising a chamber comprising a first compartment at least partially defined by a first diaphragm and having a first internal volume, a second compartment at least partially defined by a second diaphragm and having a second internal volume. The first compartment is fluidically separated from the second compartment.

A first port is provided in fluid communication with the first compartment and is configured for connection to a first conduit connected to a handheld ophthalmic cutting tool. A second port is provided in fluid communication with the second compartment, and is configured for connection to a second conduit connected to the ophthalmic cutting tool.

The first diaphragm is movably mounted with respect to the chamber, and is configured for alternate movement between a first position and a second position, such that movement of the first diaphragm from its first position to its second position decreases the first volume. The second diaphragm is movably mounted with respect to the chamber, and is configured for alternate movement between a first position and a second position, such that movement of the second diaphragm from its first position to its second position increases the second volume. Since movement of the first and second diaphragms in the first direction causes and increase in the volume of the first compartment and a decrease in the volume of the second compartment, operation of two-diaphragm aspects of the invention function in a similar manner to single-diaphragm embodiments.

To move the first and second diaphragms back and forth within the chamber to alternately vary the volume of the first and second compartments, a diaphragm actuator is coupled to the diaphragm and is configured to oscillate back and forth to simultaneously move the first and second diaphragms between the first position and the second positions. A drive system is configured to drive the oscillation of the diaphragm actuator.

In a third aspect of the invention, there is provided a surgical cutting assembly comprising an actuation system as described above and a surgical cutting tool comprising a pneumatically actuated hand-held ophthalmic cutting tool including a conduit comprising a cutting opening and a cutting blade arranged for reciprocating movement within the cutting opening. The hand-held tool comprises a reciprocatable separator fluidically separating a first sealed chamber in fluid communication with the first compartment of the actuator system from a second sealed chamber in fluid communication with the second compartment of the actuator system. The reciprocatable separator is coupled to the cutting blade and is configured for reciprocating movement in response to relative change in pressure in the first and second sealed chambers.

In any of the above described aspects of the invention, additional features may be incorporated to provide additional benefits. For example, the drive system for driving the membrane actuator can comprise a linear electric motor, such as a Lorentz motor or a reluctance motor. The electric motor can comprise an energisable coil and an array of magnets (e.g. a Hallbach array) providing a stator-mover arrangement. The energisable coil can be movable mounted with respect to a fixed Hallbach array or the Hallbach array can be movably mounted with respect to a fixed coil.

To guide the mover in linear reciprocating motion, the drive system can further comprise one or more flexible elements. The flexible element can be configured to guide the motion of the mover directly, or it can be configured to guide motion of the membrane actuator.

Optionally, the diaphragm actuator can be positioned within the chamber whilst the linear motor is position outside the chamber. In such cases, the system further comprises a coupling between the linear motor and the diaphragm actuator that extends through the wall of the chamber. Such an arrangement can allow for improved sound proofing of the oscillating membrane parts, and enhanced cooling structures (e.g. cooling fins) to dissipate heat from the electric motor.

In embodiments comprising first and second membranes, the motor can be disposed in the space in the chamber between the first and second membranes, and the coupling can extend from the motor towards the first and second membranes.

Optionally, position sensors may be employed to monitor the position of the diaphragm(s) within the chamber. For example, position sensors may be employed to directly measure the position of the diaphragm(s) and/or a position sensor may be employed to measure the position of the stator with respect to the position of the mover of the linear motor. In both cases, an optical position sensor can be used.

Pressure sensors can also be employed to determine the pressure (i) within the first and second compartments; (ii) within the first and second conduits leading to the handheld device; and/or (iii) within the first and second chambers of the reciprocator in the handle of the tool. In each case, absolute pressure sensors can be employed to measure the absolute pressure in one or more locations, or a differential pressure sensor can be employed to measure the differential pressure between two components.

Additional pneumatic components can be employed to provide enhanced functionality and safety. For example, systems according to the present invention can comprise a 'retract' valve configured to vent one of the first and second conduits upon deactivation of the motor (i.e. when the cutting mode in not in use). Venting one of the first and second fluid conduits causes the above-atmospheric pressure within the system to bias the diaphragm within the chamber 44 towards either the first position or the second position (depending on which conduit is vented). Biasing the diaphragm in towards either the first or second position means that the cutting member is either fully advanced or fully retracted with respect to the conduit. Such an arrangement can be used to ensure that the cutting opening is (substantially) not occluded during an aspiration mode (cutting mode disabled).

Further advantages of various aspect of the present invention will be apparent to the skilled person from the following description and the appended claims.

BRIEF DESCRIPTION OF THE DRAWINGS

The present invention will be described with reference to the following drawings, which illustrate non-limiting exemplary embodiments of the invention. In the drawings.

DETAILED DESCRIPTION OF ILLUSTRATIVE EMBODIMENTS

The following description provides a number of exemplary embodiments that illustrate the invention and should not be construed as limiting to the scope of the invention. Modifications or additions can be made to the illustrated embodiments without departing from the scope of the invention. It will be appreciated that the advantages associated with the present invention may be achieved by modification or replacement of the described features with equivalent features or means. Such equivalents are intended to be included within the scope of the invention. Although the present invention is described herein with reference to a vitrectomy tool comprising concentrically arranged reciprocating cutting parts, which integrally provide an aspiration conduit, it will be appreciated that the present invention can be applied to other reciprocating cutting instruments, with or without integrated aspiration.

Figure 1A:
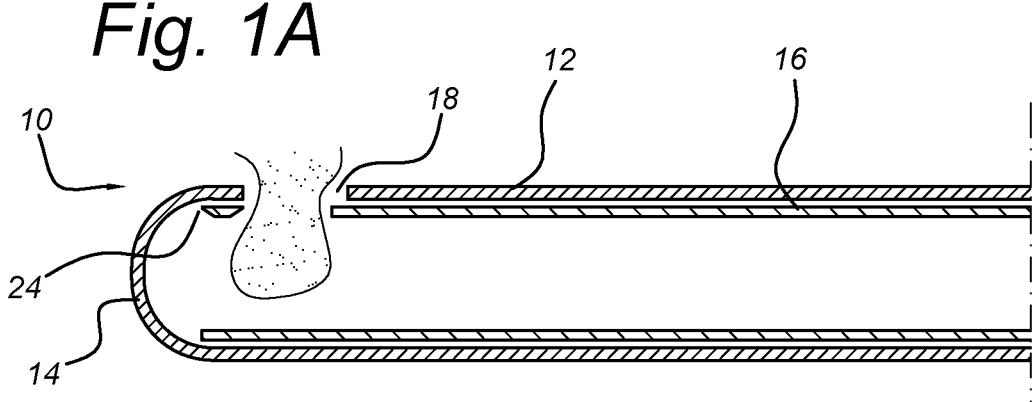
FIG. 1 shows an exemplary cutting arrangement for a vitrectomy device.
Figure 1B:
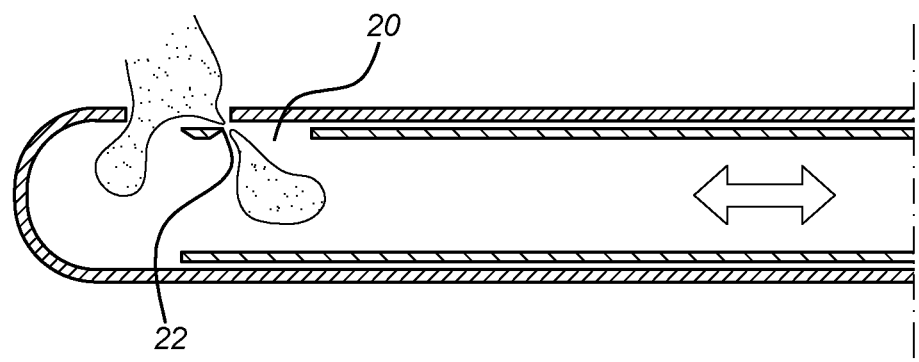
Figure 1C:
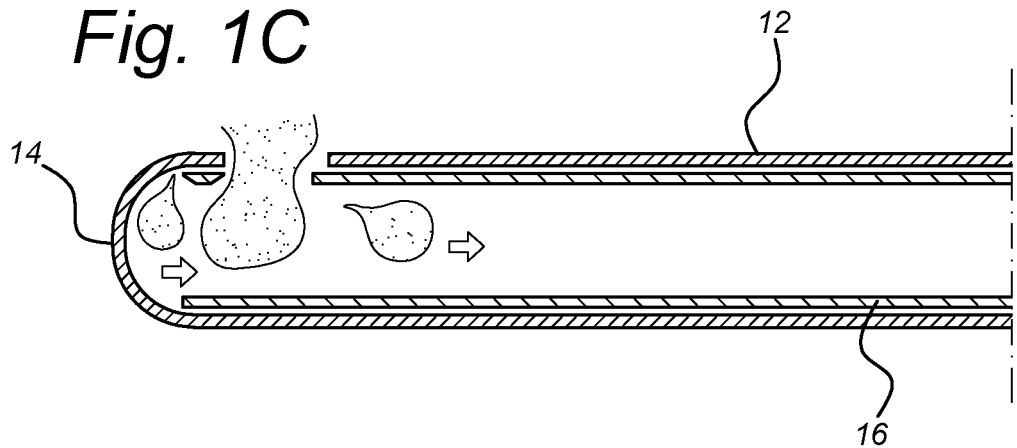

FIG. 1 shows a cutting tip of an exemplary vitrectomy device. As shown in FIG. 1, the cutting tip 10 comprises a hollow outer sheath 12, having a closed distal end 14. An inner tube 16 having an open distal end is disposed within the outer sheath 12. The inner tube 16 defines a lumen through which material can be aspirated from the eye and can thus be operatively coupled to a vacuum source (not shown) which is configured to draw material into the cutting tip 10 and through the lumen provided by the inner tube 16.

The outer sheath 12 and the inner tube 16 are configured for relative movement with respect to each other between an first 'advanced' position in which the inner tube 16 is fully advanced within the outer sheath 12 (as shown in view A of FIG. 1) and a second 'retracted' position (shown in view B of FIG. 1) in which the inner tube 16 is fully retracted with respect to the outer sheath 12.

As shown in FIG. 1, the outer sheath 12 comprises a first aperture 18 and the inner tube 16 comprises a second aperture 20. When the inner tube 16 is in the advanced position with respect to the outer sheath 12, the first and second apertures 18, 20 are aligned and in register with each other (as shown in view A). As the inner tube 16 is retracted with respect to the outer sheath 12, the second aperture 20 is retracted with respect to the first aperture 18, such a distal edge of the second aperture 20 is moves at least to a position at which it meets a proximal edge of the first aperture 18 (as shown in view B). Preferably, when the inner tube 16 is in the fully retracted position, a distal end of the inner tube is positioned proximally (towards the user) of the first aperture 18, such that the first aperture 18 is not occluded by the inner tube 16.

An edge of at least one of the first aperture 18 and the second aperture 20 forms a first cutting edge 22 such that tissue can be severed at the point where the cutting edge 22 meets an opposing surface formed by the edge of the other aperture (shown in view B). In the embodiment shown in FIG. 1, a first cutting edge 22 is formed at the distal edge of the second aperture 20 in the inner tube 16. However, the skilled person will appreciate that a cutting edge may similarly be formed at a proximal edge of the first aperture 18, or that both apertures may comprises cutting edges.

Referring now to view C of FIG. 1, a second cutting edge 24 can also be formed at the open distal end of the inner tube 16, such that tissue drawn though the first aperture 18 with the inner tube 16 in the retracted position can be severed as the inner tube 16 returns to its advanced position. The skilled person will appreciate that a cutting edge can alternatively or additionally be formed at the distal edge of the first aperture 18.

Figure 2:
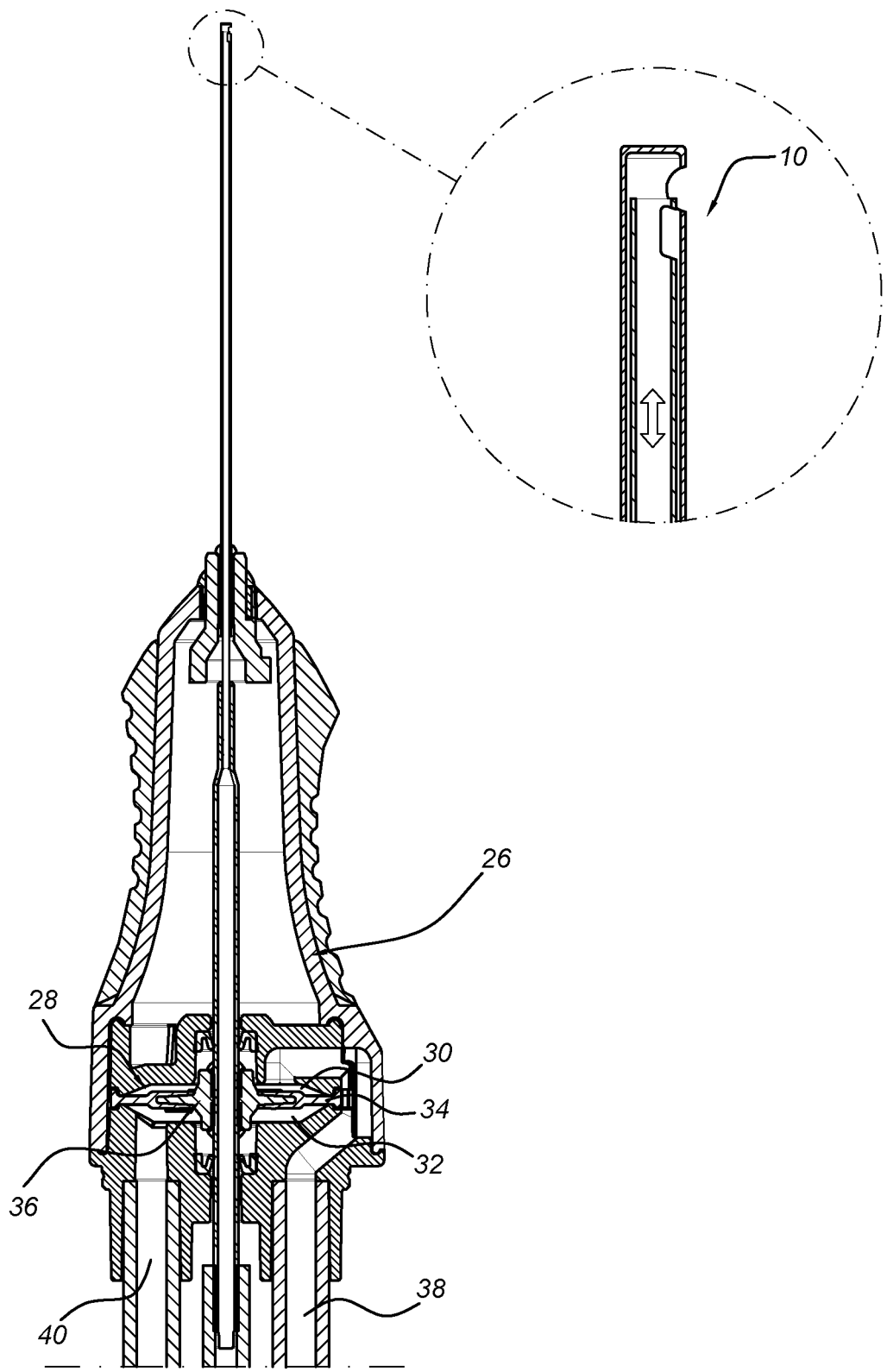
FIG. 2 shows a handheld vitrectomy tool, comprising a pneumatic actuator.

Oscillation of the cutting tip 10 can be controlled pneumatically. Referring now to FIG. 2, the handheld portion of a vitrectomy tool is shown. As shown in FIG. 2, the handheld portion of the tool comprises the cutting tip 10 described with reference to FIG. 1 and a housing 26. The housing 26 is shaped and sized for one-handed use by a healthcare professional, and comprises a generally elongate shape. The outer sheath 12 and the inner tube 16 extend into the housing 26. As shown in FIG. 2, the outer sheath 12 is fixed with respect to the housing 26, whilst the inner tube 16 is slidably mounted therein. The inner tube 16 is operatively coupled to a reciprocator assembly 28, which is configured to oscillate back and forth to drive reciprocal movement of the inner tube 16 with respect to the sheath 12 in a cutting action, as described with reference to FIG. 1.

The reciprocator assembly 28 comprises a first chamber 30 and a second chamber 32 fluidically separated from each other by a flexible membrane or separator 34. The separator 34 comprises a linkage or coupling 36, which couples the separator 34 to the inner tube 16. The first chamber 30 is in fluid communication with a first conduit or pneumatic line 38 and the second chamber 32 is in fluid communication with a second conduit or pneumatic line 40. To drive oscillation of the separator 34 (and thus the inner tube 16) back and forth, the pressure within the first and second chambers 30, 32 is alternately increased and decreased. When the pressure differential between the first chamber 30 and the second chamber 32 biases the flexible membrane in a distal direction, the inner tube 16 moves distally with respect to the fixed outer sheath 12. When the pressure differential between the first chamber 30 and the second chamber 32 biases the membrane 34 in a proximal direction, the inner tube 16 moves proximally with respect to the outer sheath 12. The pressure differential between the first chamber 30 and the second chamber 12 is controlled via the first and second pneumatic lines 38, 40.

Figure 3:
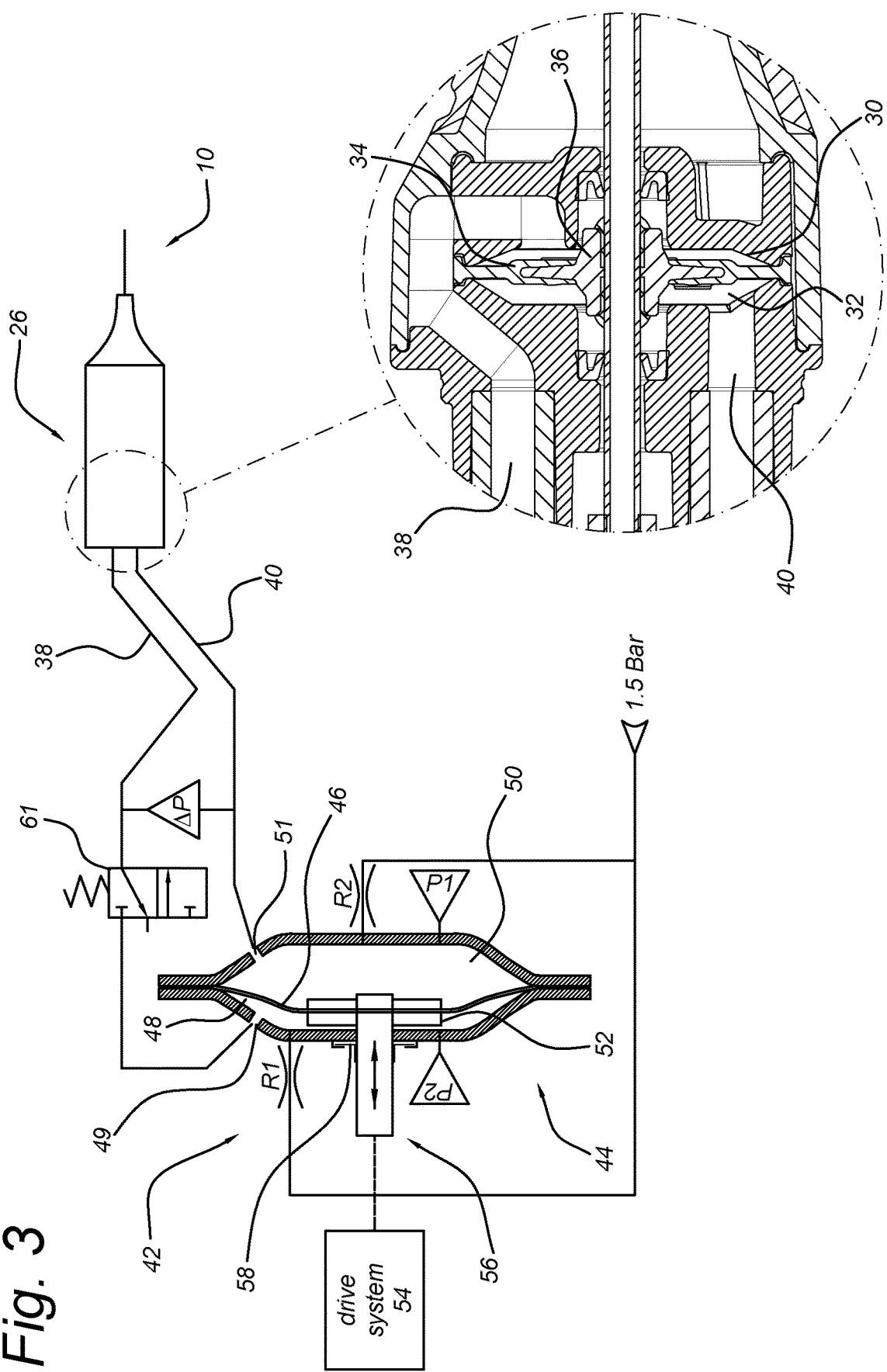
FIG. 3 shows a schematic view of a vitrectomy system comprising a handheld vitrectomy tool, a pneumatic actuation system and a control loop.

Referring now to FIG. 3, the pneumatic lines 38, 40 are coupled to an actuation system 42 that alternately varies the pressure within the first and second chambers 30 and 32. As shown in FIG. 3, the system 42 comprises a housing forming a chamber 44, which is fluidically separated by a diaphragm 46 into a first compartment 48 defining a first internal volume and a second compartment 50 defining a second internal volume. A first port 49 is provided in fluid communication with the first compartment 48 and is configured for connection to a first conduit 38. A second port 51 is provided in fluid communication with the second compartment 50, and is configured for connection to a second conduit 40.

The diaphragm 46 is movably mounted within the chamber 44. The diaphragm can be formed of a flexible material (such as a thermoplastic elastomer or a rubber) and/or it may be fixed within the chamber with some slack to allow reciprocating movement. In any event, the diaphragm 46 shown in FIG. 3 is configured for alternate movement between a first position and a second position, such that movement from the first position to the second position decreases the first volume (in the first compartment 48) and increases the second volume (in the second compartment 50). Conversely, movement of the diaphragm 46 in the opposite direction, from the second position to the first position, increases the volume of the first compartment 48, and decreases the volume of the second compartment 50. The system further comprises a diaphragm actuator 52 configured to oscillate back and forth to move the diaphragm 46 between the first position and the second position and a drive system 54 configured to drive the oscillation of the diaphragm actuator 52.

To drive the diaphragm actuator 52 back and forth, the drive system 54 can comprise a linear motor. In some embodiments, the linear motor is linear oscillator motor configured to drive the diaphragm 46 back and forth at a desired frequency in response to an alternating control current or voltage supplied to the motor. In exemplary embodiments, the driver 54 can comprise a Lorentz-type actuator, also known as a Lorentz driver, e.g. implemented using a Tecnotion UL series linear motor. In other embodiments, the driver 54 can comprise a reluctance motor. Further details of the driver 54 will be described below with reference to FIG. 6.

Each of the first and second compartments 48, 50 can be coupled to an above-ambient air supply. For example, as shown in FIG. 3, each of the first and second compartments can be in fluid communication with a 1.5 bar air supply, e.g. via flow-restrictions $R_1$ and $R_2$. By providing the first and second compartments with above-atmosphere air supply, the stiffness of the 'gas spring' that drives the reciprocator in the handle housing 26 is increased, improving the responsiveness of the pneumatic system. Moreover, above atmospheric pressure within the first and second compartments 48, 50 can allow the diaphragm to be biased into the first or second position if one of the compartments 48, 50 or one of the pneumatic lines 38, 40 is vented. It is worth noting that the complete pneumatic system is a closed volume, and part of it is only vented when the retract valve 61 (see below) is opened. Therefore the air consumption of the total system is low, and a very small built-in compressor can suffice for the air supply, removing the need for an external air-supply line.

As shown in FIG. 3, a control loop can be implemented to provide the desired pressure levels within the first and second compartments 48, 50 (and thus within the chambers 30 and 32 of the handheld tool). The control loop can comprise an alternating current or voltage supply configured to drive the linear motor back and forth. The control loop can drive the actuator at an oscillating frequency of between 5-200 Hz, e.g. 166 Hz. This allows for a handheld vitrectomy tool that is operable at 10.000 movement per minute or more. The skilled person will appreciate that the oscillating frequency of the drive system 54 can continuously be varied depending on the requirements of the procedure, the architecture of the handheld device and the preference of the health care provider.

To provide improved control of the actuator, the control loop can further comprise one or more sensors to determine the oscillation of the diaphragm 46 within the chamber 44.

For example, a position sensor can be integrated to measure the position of the diaphragm 46 within the chamber 44. The position of the diaphragm 46 provides information regarding the relative volumes of the first and second compartments 48, 50, and thus the pressures supplied via pneumatic lines 38, 40.

Additionally or alternatively, one or more pressure sensors can be incorporated into the actuation system. For example, as shown in FIG. 3, a pressure sensor P1 can be provided in fluid communication with the first compartment 48 to measure the pressure within the first compartment 48 and the first pneumatic line 38. Additionally or alternatively, a pressure sensor P2 can be provided in fluid communication with the second compartment 50 to measure the pressure within the second compartment and the second pneumatic line 40. As an alternative to or in combination with P1 and/or P2, a differential pressure sensor ΔP can be provided to measure the differential pressure between the first pneumatic line 38 and the second pneumatic line 40. The differential pressure sensor can be implemented to measure the differential pressure between the first and second compartments 48, 50, or it can be implemented to measure the differential pressure between the first and second conduits 38, 40, close to the handheld device.

The pressure sensors connected to each compartment allow monitoring of the achieved pressure difference between the first and second compartments 48, 50. Each pressure sensor, alone or in combination, can allow verification for proper functioning and can be used for controller feedback.

In at least some embodiments, the actuation system further comprises a retract valve 61 configured to move the diaphragm 34 to the first position upon deactivation of the drive system. Such a retract valve arrangement can advantageously allow the neutral position of the diaphragm to correspond to an intermediate position of the inner tube 16 with respect to the outer sheath 12, without compromising the aspiration flow through the cutting opening whilst the cutting blade is at rest (with the motor deactivated). This is because the retract valve vents one compartment/pneumatic line whilst the other is maintained at 1.5 bar. The pressure differential thus biases the diaphragm towards the first position whilst the cutting mode is switched off, even though the neutral position of the membrane equates to an intermediate position of the inner tube 16 with respect to the outer sheath 12. Such a neutral rest position allows for a short stroke for the inner tube 16, and consequently a short stroke for the motor. Such a retract valve 61 could be a regular 3/2 solenoid valve shown in FIG. 3, or alternatively a set of 2/2 solenoid valves, arranged such that conduit 38 can be vented to ambient pressure, and the supply from volume 48 can be blocked.

To ensure that the pressure within the first and second compartments 48, 50 does not exceed a predetermined level, vent valves can also be provided to vent gas from the first and second compartments 48, 50 at a predetermined pressure level or within a predetermined pressure range. An exemplary pneumatic system comprising a series of vent valves and a retract valve will be described in more detail with reference to FIG. 7.

The arrangement of the driver 54 and the chamber 44 will now be described in more detail with reference to FIG. 4.

Figure 4:
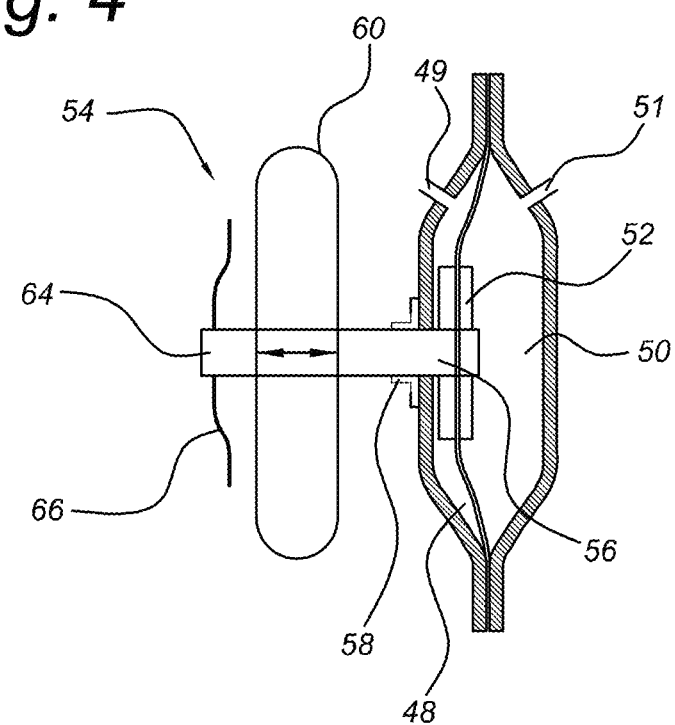
FIG. 4 shows a schematic view of an actuation system in accordance with a first embodiment of the invention.

As shown in FIG. 4, the driver 54 can comprises a coil 60 configured to be energised by an applied current or voltage, and an array of magnets 62 (e.g. a Hallbach array). The array of magnets can be configured as the stator, or it can be configured as mover in the drive system 54 of the present invention.

A guide element, for example a flexible element such as a radial spring 66, is provided to guide the mover in reciprocating linear motion. The moving part of the motor (the array or the coil) is coupled to the diaphragm actuator 52 directly or via a linkage 56.

As shown in FIG. 4, the diaphragm actuator 52 is positioned within the chamber 44. The diaphragm actuator 52 can engage the membrane 46 in different ways. For example, the diaphragm actuator 52 can be securely fastened to the diaphragm with adhesive, or it may comprise opposing parts between which the diaphragm is clamped. Alternatively, the diaphragm actuator 52 can be partially embedded within the material of the diaphragm 46.

The stator is positioned outside of the chamber 44, and a coupling 56 extends through a wall of the chamber 44 into the first compartment 48. A seal 58 seals the opening in the chamber wall through which the coupling 56 extends. In some embodiments, an additional opening (not shown) can be provided in second compartment 50, comprising a seal similar to seal 58. The additional opening can be provided to approximate or mirror the leakage experienced through the seal 58, to offset any imbalance in the pressure due to leakage from the first compartment 48.

The skilled person will appreciate that the coupling between the membrane actuator 52, the coupling 56, and the mover can be adapted to suit the requirements of the system, and that these components may also be formed as a single part.

Figure 5:
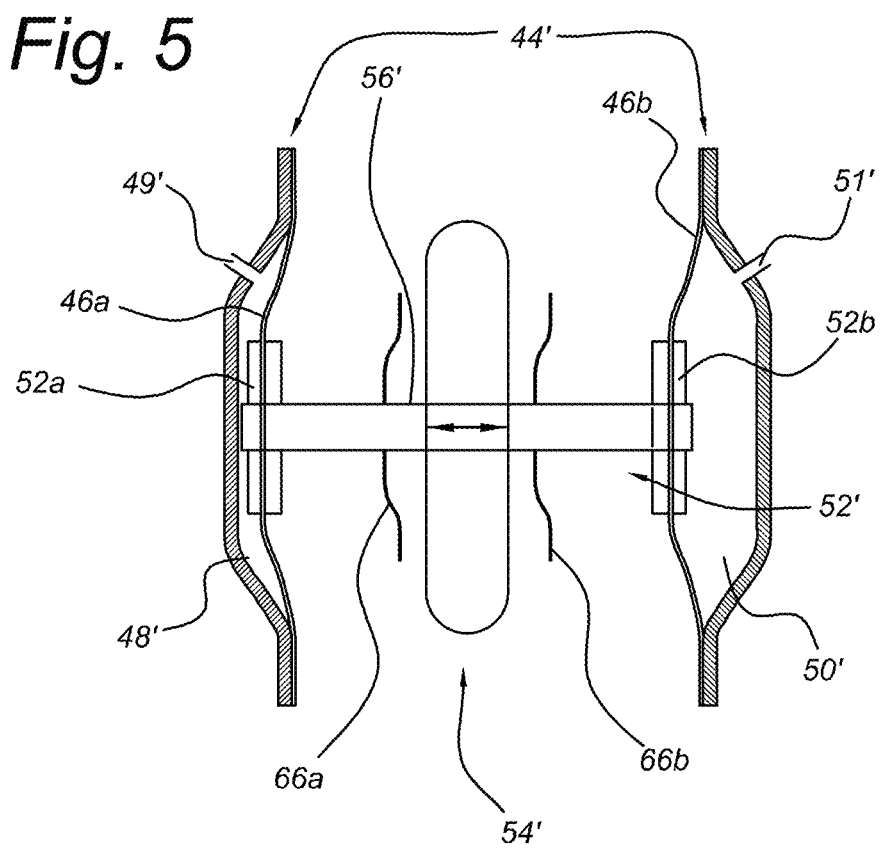
FIG. 5 shows a schematic view an actuation system in accordance with a second embodiment of the invention.

FIG. 5 shows a further aspect of the invention in which the configuration of the driver 54 and the first and second compartments 48, 50 differs from the arrangement shown in FIG. 4.

As shown in FIG. 5, an ophthalmic cutting tool actuation system in accordance with a second aspect of the invention comprises a housing 44' having a first compartment 48' at least partially defined by a first diaphragm 46a and having a first internal volume. A second compartment 50' is at least partially defined by a second diaphragm 46b and has a second internal volume.

A first port is provided in fluid communication with the first compartment 48' and is configured for connection to a first conduit connected to a handheld ophthalmic cutting tool, in the manner described in connection with FIGS. 2 and 3. Similarly, a second port is provided in fluid communication with the second compartment 50', and is configured for connection to a second conduit connected to the ophthalmic cutting tool.

The first diaphragm 46a is movably mounted with respect to the housing 44', and is configured for alternate movement between a first position and a second position, such that movement of the first diaphragm 46a from its first position to its second position decreases the first volume of the first compartment 48'. The second diaphragm 46b is similarly movably mounted with respect to the housing 44', and is configured for alternate movement between a first position and a second position, such that movement of the second diaphragm 46b from its first position to its second position increases the second volume of the second compartment 50'.

The system further comprises a diaphragm actuator 52' configured to oscillate back and forth to move the first diaphragm 46a and the second diaphragm 46b simultaneously between the first position and the second position. A drive system 54', disposed within the housing 44' in the embodiment shown in FIG. 5, is configured to drive the oscillation of the diaphragm actuator 52'.

Simultaneous movement of the diaphragm actuator 52' back and forth within the housing 44' moves the first and second diaphragms 46a, 46b back and forth in unison, alternately increasing and decreasing the interior volumes of the first and second compartments 48', 50', in a similar manner to the single diaphragm embodiment described with reference to FIG. 4. The two diaphragms acting in unison operate in an equivalent manner to the single diaphragm of FIG. 4.

As shown in FIG. 5, the first and second diaphragms 46a, 46b can be separated by a space within the housing 44', and the drive system 54' can be at least partially disposed within the space between the first and second diaphragms 46a, 46b. This provides a simple construction for the actuator 52' and allows reciprocating movement of the motor to the transmitted directly to the parts 52a, 52b of the diaphragm actuator 52'.

The drive system 54' can be configured in a similar manner to the drive system 54 described with reference to FIG. 4 and can comprise a linear motor comprising a coil and a Hallbach array. The motor can comprise a Lorentz driver or a reluctance motor.

The diaphragm actuator 52' can comprise multiple parts or can be formed as a single piece, driven by the mover. In the embodiment shown in FIG. 5, the diaphragm actuator 52' comprises a first diaphragm actuator 52a that clamps the first diaphragm 46a, and a second diaphragm actuator 52b that clamps the second diaphragm 46b. A common coupling 56' can fixedly connect the two parts 52a, 52b. The common coupling can be integrally formed with or connected to the mover actuator of the motor.

In the embodiment shown in FIG. 5, the drive system 54 comprises first and second flexible guiding element 66a, 66b to guide the linear motion of the actuator.

The actuator and chamber assembly shown in FIG. 5 can be combined with the control loop described with reference to FIG. 5. For example, a control loop can be provided that comprising a position sensor configured to monitor the position of at least one of the first and second diaphragms within the housing.

Additionally or alternatively, pressure sensors can be provided to measure the pressure within one or both of the first and second compartments 48', 50'. The system can comprise a first pressure sensor configured to measure the pressure within the first compartment and a second pressure sensor configured to monitor the pressure within the second compartment.

First and second vent valves can also be provided in the arrangement shown in FIG. 5, to vent the first and second compartments 48', 50' should a predetermined maximum pressure be reached.

As shown in FIG. 3, a differential pressure sensor can be provided to measure the differential pressure between the first and second compartments. A retract valve 61 can also be incorporated into the system shown in FIG. 5 (similar as in the embodiment described with reference to FIG. 3 above), configured to move the diaphragm 34 (and the inner tube 16) to its respective first position upon deactivation of the drive system.

Figure 6:
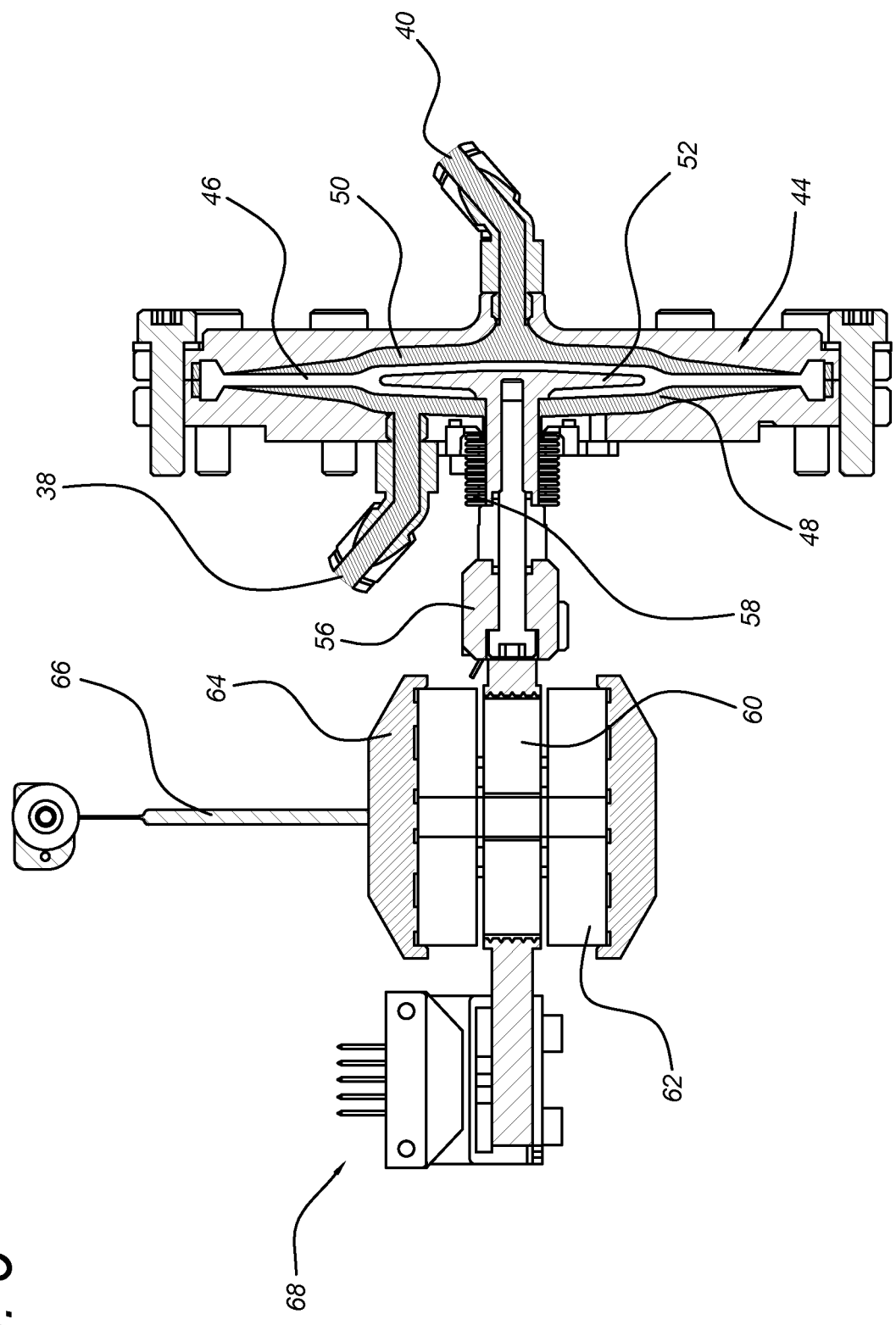
FIG. 6 shows a detailed cross-sectional view of an actuation system according to the present invention.

FIG. 6 shows in more detail a drive system 54 and a chamber 44 in accordance with an embodiment of the present invention. As shown in FIG. 6, the drive system 54 comprises a linear motor having a mover-coil 60 and a Hallbach array 62 forming the stator. The magnets of the Hallbach array are mounted on back-irons 64. The mover-coil 60 is coupled via linkage 56 to the diaphragm actuator 52, which in the embodiment shown in FIG. 6 is partially embedded within the material of the diaphragm 46.

An optical sensor 68 is configured to measure the position of the stator 62 relative to the coil 60, and thus the position of the diaphragm actuator 52 within the chamber 44. Straight-guidance flexures 66 are fixedly coupled to the mover-coil 60 to ensure that the mover-coil moves back and forth in a straight line. The mover-coil 60 can further comprise cooling fins to dissipate heat generated during use.

As shown in FIG. 6, the chamber 44, diaphragm 46 and diaphragm actuator 52 can be configured to minimise the air-volume within the first and second compartments 48, 50. The minimised chamber volume results in the largest compression ratio (ratio of neutral volume to compressed volume).

The stroke of the motor in the exemplary embodiment shown in FIG. 6 is approximately 4 mm (2 mm in a first direction from a neutral rest position, and 2 mm in an opposite direction away from the neutral rest position). The total air volume of the chamber (consisting of the air volume of the first and second compartments) is approximately 20 ml. Such a configuration allows a maximum differential pressure within the first and second compartments of the chamber of approximately 1000 mbar, while the preferred working range is between 300 and 700 mbar.

In the embodiment shown in FIG. 6, the seal 58 comprises a sealing bellow. The sealing bellow allows the motion of the coupling 56 to be transferred through the chamber wall to the diaphragm 46, without sliding components and without leakage.

Figure 8:
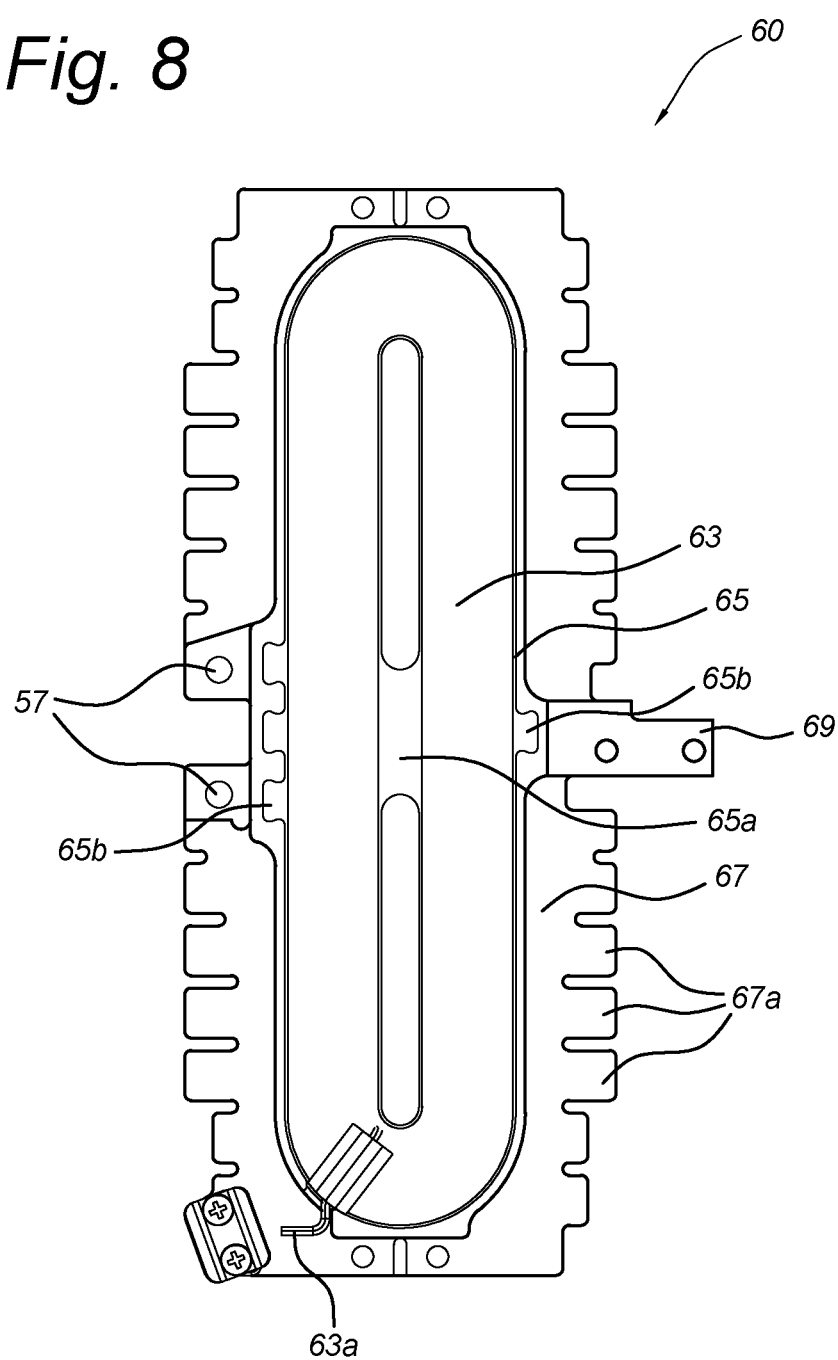
FIG. 8 shows a side view of an exemplary embodiment of a motor assembly applied in an actuation system according to the present invention.

FIG. 8 shows a side view of an exemplary embodiment of the mover-coil 60 as can be used in the present invention drive system 54. Together with a set of permanent magnets (e.g. as part of the stator 62 as described above), this mover-coil 60 forms the motor that drives the present invention actuation system embodiments. The mover-coil 60 comprises a (flat wound) coil 63 which is wound around a core (not visible in FIG. 8), and then inserted in an aluminum frame 67. It is then filled with a casting resin, forming a casting compound 65, and the core is removed. Connection leads 63a are provided at the bottom of the coil 63 in the embodiment shown. The frame 67 comprises attachment points 57 for the coupling 56 to the diaphragm actuator 52, as well as an extension 69 for cooperation with the (optical) sensor 68.

The casting compound 65 comprises several extensions 65b into the frame 67 for providing a rigid structure, as well as a bridge part 65a which is provided in the center at the height of the attachment points 57. The bridge part 65a allows forces to be transferred in-line with the point where the forces act, without adding too much mass. Additionally, the frame 67 is provided with cooling fins 67a, having a cutout up to a maximum of halfway the width of the frame 67 such that the motor frame 67 is stiffer and can support the forces better.

The structure of the mover-coil 60 having the bridge part 65a in the center of casting compound 65 effectively prevent damage to the mover-coil 60. As a side effect a much lower acoustic noise production at the same motor amplitude is provided. This is accomplished by the combination of frame 67 and casting compound 65 having a stiffer structure, such that the parasitic vibrations (other than the linear motion in the direction along coupling 56), have a much lower amplitude. The lower noise level is beneficial for the user who works for long periods near the actuation system of the present invention. A further advantage is that the drive system 54 amplitude (and therefore the actuation pressure to the instrument) can be increased, without producing excessive noise levels.

Figure 7:
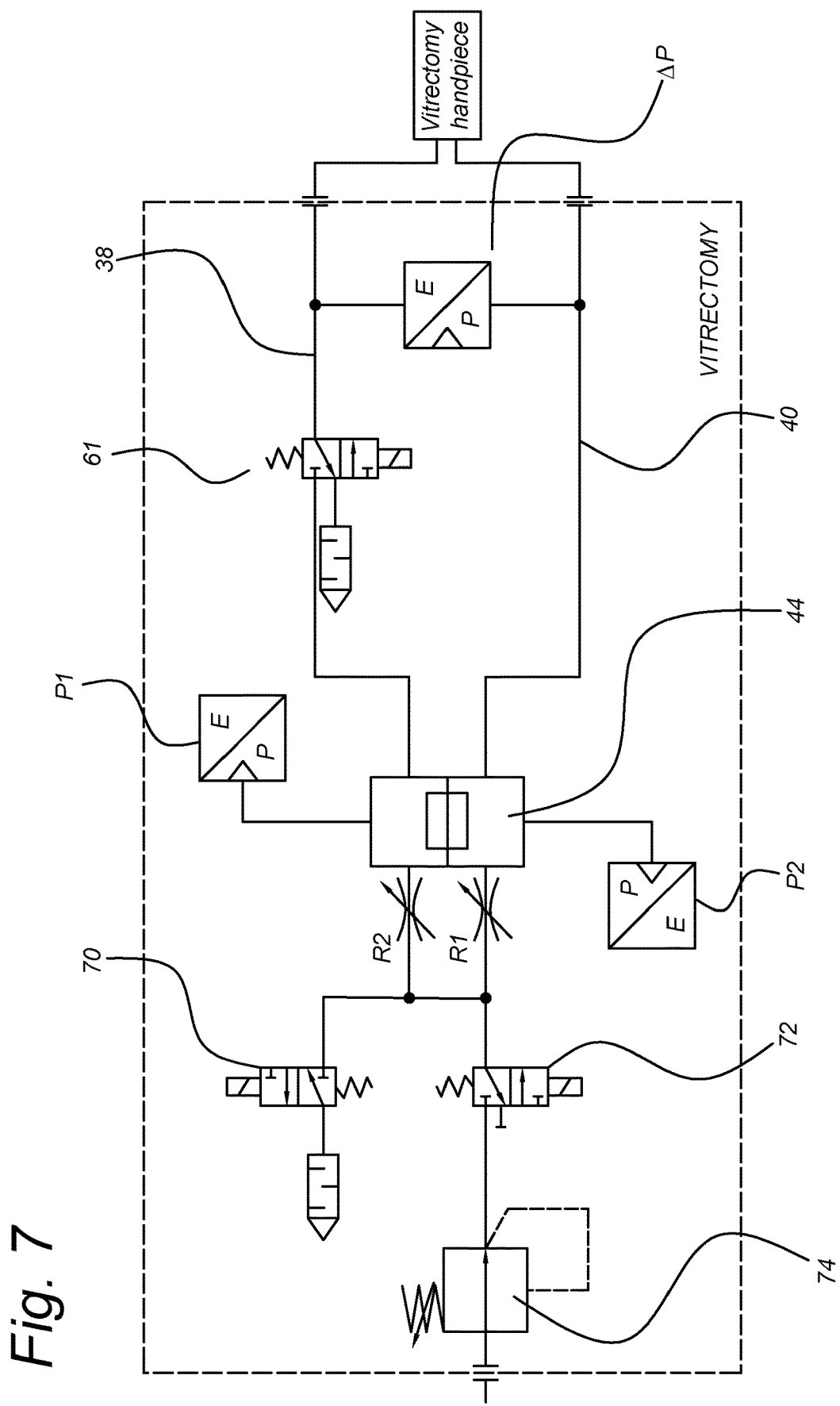
FIG. 7 shows a pneumatic diagram for an exemplary control loop.

Referring now to FIG. 7, an exemplary embodiment of a pneumatic control system will be described in more detail. As shown in FIG. 7, the control system comprises pressure sensors P1 and P2, in fluid communication with the first and second compartments of chamber 44 respectively. Pressure sensors P1 and P2 are absolute pressure sensors. Differential pressure sensor ΔP is arranged between the first and second pneumatic lines 38, 40 and is configured to monitor the differential pressure within the system. By configuring the differential pressure sensor ΔP to measure the differential pressure between the first and second pneumatic lines 38, 40, the achieved pressure differential close to the reciprocator 28 is observed.

A bias pressure inlet 74 comprising a pressure regulator is also provided to supply above-atmospheric pressure supplied to the chamber 44 (e.g. 1.5 bar). The above atmospheric pressure leads to increased stiffness of the effective gas spring that drives the reciprocator 28 within the handheld device. A bias pressure inlet valve 72 and a bias pressure vent valve 70 are provided to apply the bias pressure before use, and vent it to a safe state after use respectively. In exemplary embodiments, the supply to the chamber 44 is maintained at 1.5 bar. An allowable error range in this respect would be 0 . . . +0.2 mbar, i.e. 1.5 to 1.7 bar.

A retract valve 61 can be provided in fluid communication with one of the first and second pneumatic lines 38, 40. In the system shown in FIG. 6, the retract valve 61 is provided in communication with the first pneumatic line. The retract valve 61 is configured to vent one of the pneumatic lines 38, 40. The bias pressure supplied by the system through the other (un-vented) pneumatic line pushes the actuator in the hand-held device to one end (see FIGS. 1A-C) to ensure that the first aperture in the outer sheath is not occluded by the inner sheath, thereby allowing maximum flow through the inner tube when a cutting action is not used. As an exemplary implementation, an SMC VDW 250 3/2 valve is applied, which is a commercially available valve. In some embodiments, the retract valve 61 is configured to bias the diaphragm 46 in a direction that results in retraction of the inner tube 16 to its maximum extent within the outer sheath 12 when the cutting operation is ceased. However, the skilled person will appreciate that the retract valve 61 can be configured to bias the inner tube 16 distally towards its maximum distal extent. In either embodiment, the extreme distal or extreme proximal location of the inner tube 16 relative to the outer sheath 12 means that the first opening 18 in communication with the aspiration lumen is (substantially) not occluded to allow free flow of material (including severed material and fluid) through the lumen of the inner tube 16.

It will be appreciated that the drive system described with reference to FIG. 6 and the control loop described with reference to FIG. 7 can be employed in combination with either of the chamber assemblies described with reference to FIGS. 4 and 5. Other structural arrangements comprising two variable volume chambers that can be combined with the exemplary drive system 54 will be apparent to the person skilled in the art in light of the present disclosure, and such arrangements are intended to fall within the scope of the present invention.

The foregoing description provides a number of exemplary embodiments that illustrate the invention and should not be construed as limiting to the scope of the invention. Modifications or additions can be made to the illustrated embodiments without departing from the scope of the invention. Although the present invention is described herein with reference to a vitrectomy tool comprising concentrically arranged reciprocating cutting parts, with integrated aspiration, it will be appreciated that the present invention can be applied to other reciprocating instruments.

The invention claimed is:

1. An actuation system for an ophthalmic cutting tool, the actuation system comprising:
   a housing comprising a chamber fluidically separated by a diaphragm into a first compartment defining a first internal volume and a second compartment defining a second internal volume, wherein the diaphragm is moveably mounted within the chamber and configured for alternate movement between a first position and a second position such that movement from the first position to the second position decreases the first volume and increases the second volume;
   a first port in fluid communication with the first compartment that is configured for connection to a first conduit connected to the ophthalmic cutting tool;
   a second port in fluid communication with the second compartment that is configured for connection to a second conduit connected to the ophthalmic cutting tool;
   a diaphragm actuator secured to the diaphragm and configured to oscillate back and forth to move the diaphragm between the first position and the second position, and
   a drive system configured to drive the oscillation of the diaphragm actuator,
   wherein the ophthalmic cutting tool comprises a reciprocator assembly comprising a first sealed chamber in fluid communication with the first conduit, a second sealed chamber in fluid communication with the second conduit, and a reciprocating separator that is arranged to fluidly separate the first and second sealed chambers and is driven to oscillate by a pressure differential between the first and second sealed chambers.

2. The system according to claim 1, wherein the drive system comprises a linear motor configured to drive the diaphragm actuator in at least a first direction.

3. The system according to claim 2, wherein the drive system further comprises a flexible element configured to guide the linear motion of the diaphragm actuator.

4. The system according to claim 3, wherein the linear motor is positioned outside the chamber, and the drive system further comprises a coupling between the linear motor and the actuator that extends through a wall of the chamber.

5. The system according to claim 1, wherein the diaphragm actuator is positioned within the chamber.

6. The system according to claim 1, further comprising a position sensor configured to monitor the position of the diaphragm within the chamber.

7. The system according to claim 1, further comprising a first pressure sensor configured to measure pressure within the first compartment and/or a second pressure sensor configured to measure pressure within the second compartment.

8. The system according to claim 1, further comprising a differential pressure sensor configured to measure differential pressure between the first compartment and the second compartment.

9. The system according to claim 1, further comprising a retract valve configured to vent a first pneumatic line to move the diaphragm to the first position upon deactivation of the drive system.

10. The system according to claim 1, wherein one or both of the first compartment and the second compartment comprises a respective vent valve.

11. A surgical cutting assembly comprising the actuation system of claim 1, wherein the ophthalmic cutting tool is pneumatically actuated and further comprises
a conduit comprising a cutting opening; and
a cutting blade arranged for reciprocating movement within the cutting opening, wherein the reciprocating separator is coupled to the cutting blade.

12. The system according to claim 1, wherein the diaphragm actuator is partially embedded in the diaphragm; or the diaphragm actuator comprises opposing parts configured to clamp the diaphragm therebetween; or the system further comprises an adhesive adapted to securely fasten the diaphragm actuator to the diaphragm.

13. An actuation system for an ophthalmic cutting tool, the actuation system comprising:
a housing comprising:
a first compartment at least partially defined by a first diaphragm and having a first internal volume, wherein the first diaphragm is movably mounted with respect to the housing and is configured for alternate movement between a first position and a second position such that movement from the first position to the second position decreases the first volume;
a second compartment fluidly separated from the first compartment and at least partially defined by a second diaphragm and having a second internal volume, wherein the second diaphragm is movably mounted with respect to the housing and is configured for alternate movement between a third position and a fourth position such that movement from the third position to the fourth position increases the second volume;
a first port in fluid communication with the first compartment that is configured for connection to a first conduit connected to the ophthalmic cutting tool;
a second port in fluid communication with the second compartment that is configured for connection to a second conduit connected to the ophthalmic cutting tool;
a diaphragm actuator comprising a first diaphragm actuator member and a second diaphragm actuator member fixedly coupled to each other with a coupling, the diaphragm actuator configured to oscillate back and forth to move the first diaphragm between the first position and the second position and the second diaphragm between the third position and the fourth position simultaneously, and
a drive system configured to drive the oscillation of the diaphragm actuator,
wherein the ophthalmic cutting tool comprises a reciprocator assembly comprising a first sealed chamber in fluid communication with the first conduit, a second sealed chamber in fluid communication with the second conduit, and a reciprocating separator that is arranged to fluidly separate the first and second sealed chambers and is driven to oscillate by a pressure differential between the first and second sealed chambers.

14. The system according to claim 13, wherein the drive system comprises a linear motor configured to drive the diaphragm actuator in at least a first direction.

15. The system according to claim 14, wherein the drive system further comprises at least one flexible element configured to guide the linear motion of the diaphragm actuator.

16. The system according to claim 14, wherein the first and second diaphragms are separated by a space within the housing, and the linear motor is at least partially disposed within the space between the first and second diaphragms.

17. The system according to claim 13, further comprising a position sensor configured to monitor the position of at least one of the first and second diaphragms within the housing.

18. The system according to claim 13, further comprising a first pressure sensor configured to measure pressure within the first compartment and a second pressure sensor configured to monitor pressure within the second compartment.

19. The system according to claim 13, wherein one or both of the first compartment and the second compartment comprises a respective vent valve.

20. The system according to claim 13, further comprising a differential pressure sensor configured to measure differential pressure between: the first compartment and the second compartment; and/or the first conduit and the second conduit.

21. The system according to claim 13, further comprising a retract valve configured to move either the first diaphragm to the first position or the second diaphragm to the third position upon deactivation of the drive system.

* * * * *